US00PP09377P

United States Patent [19]

Hammons

[11] Patent Number: Plant 9,377

[45] Date of Patent: Nov. 21, 1995

[54] *MAGNOLIA GRANDIFLORA* NAMED 'GREEN GIANT'

[75] Inventor: Bruce Hammons, Trussville, Ala.

[73] Assignee: Plantation Tree Company, Selma, Ala.

[21] Appl. No.: 264,502

[22] Filed: Jun. 23, 1994

[51] Int. Cl.[6] ..... A01H 5/00

[52] U.S. Cl. ..... Plt./53.5

[58] Field of Search ..... Plt./53.5

[56] References Cited

U.S. PATENT DOCUMENTS

P.P. 2,250 4/1963 Wallner et al. ..... Plt./53.5

*Primary Examiner*—James R. Feyrer

*Attorney, Agent, or Firm*—Cushman Darby & Cushman

[57] ABSTRACT

A new southern magnolia for the grandiflora variety distinguished by its rapid dense growth and large glossy leaves which are green on both sides and exhibit minimal pubescence, as well as the coarse, textured, broad, blunt, flame shape tree and dense foliage with a strong, dominant central leader.

2 Drawing Sheets

BACKGROUND OF THE NEW PLANT

My new variety of *Magnolia grandiflora* was discovered and first observed in a bed of *Magnolia grandiflora* (southern magnolia) seedlings at the Westervelt Tree Company in Selma, Ala. These seedlings were among a group of one gallon seedlings previously obtained from the Powell Nursery, Thomasville, Ga., and planted at Westervelt Tree Co. in 1984. The parent trees and the source of the seed are unknown.

This new variety was initially reproduced in 1986 at the Westervelt Tree Company in Selma, Ala. Subsequently, a considerable number of selected cuttings were rooted and grown to test the stability, uniformity and growth rate of the clonal material. Since 1986, this new plant has been propagated by rooted cuttings of the current season's growth through several generations, and we have been able to thereby determine that the novel and distinctive features of the new cultivar, *Magnolia grandiflora* "Green Giant", plant have remained true from generation to generation and appear to have been firmly fixed.

DESCRIPTION OF THE DRAWINGS

Our new *Magnolia grandiflora,* and certain features thereof, are illustrated by the accompanying color drawings (photographs).

Figure 1:
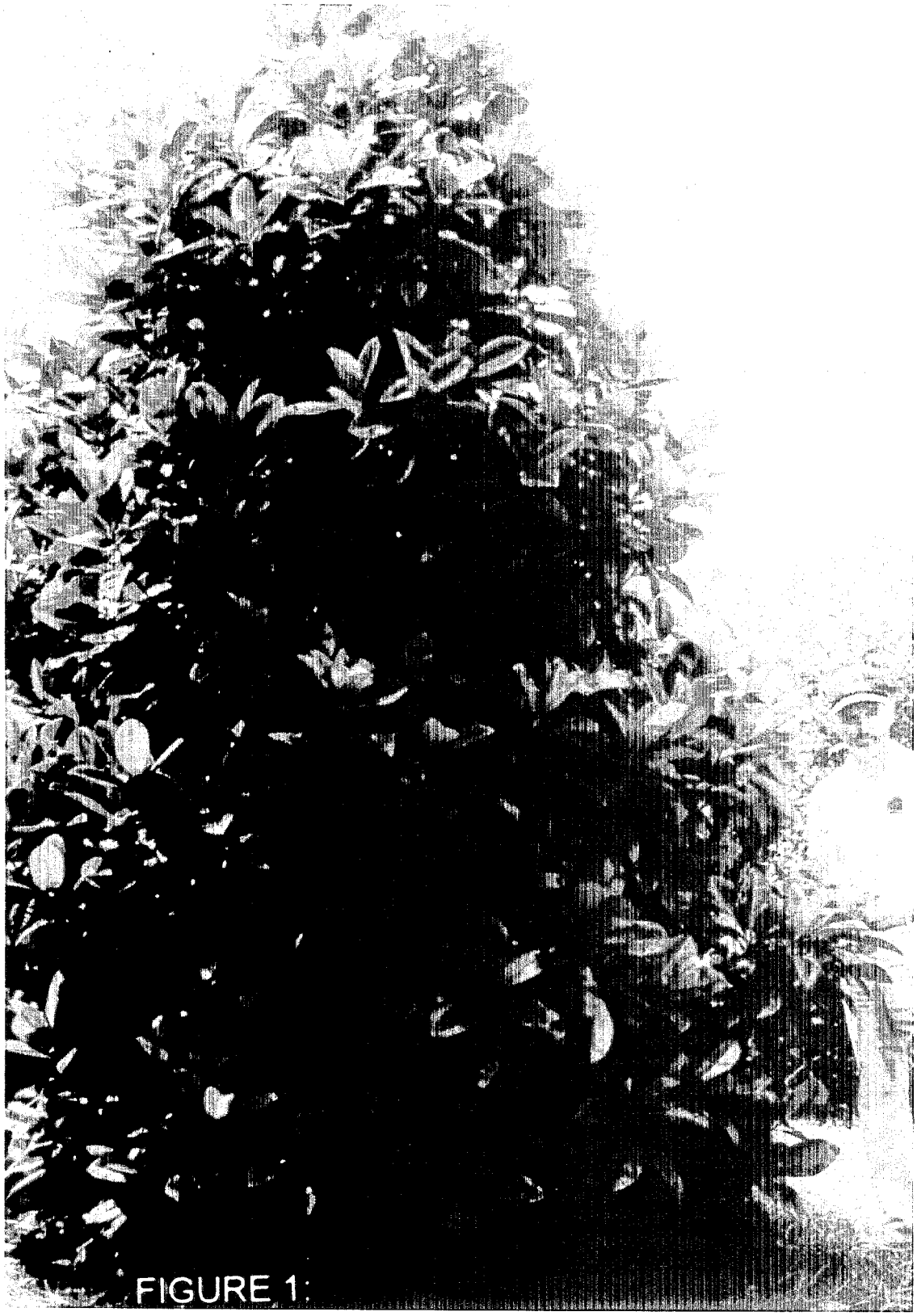
FIG. 1 is a photograph showing a tree that is about 6 years old and about 10 to 12 feet tall.
Figure 2:
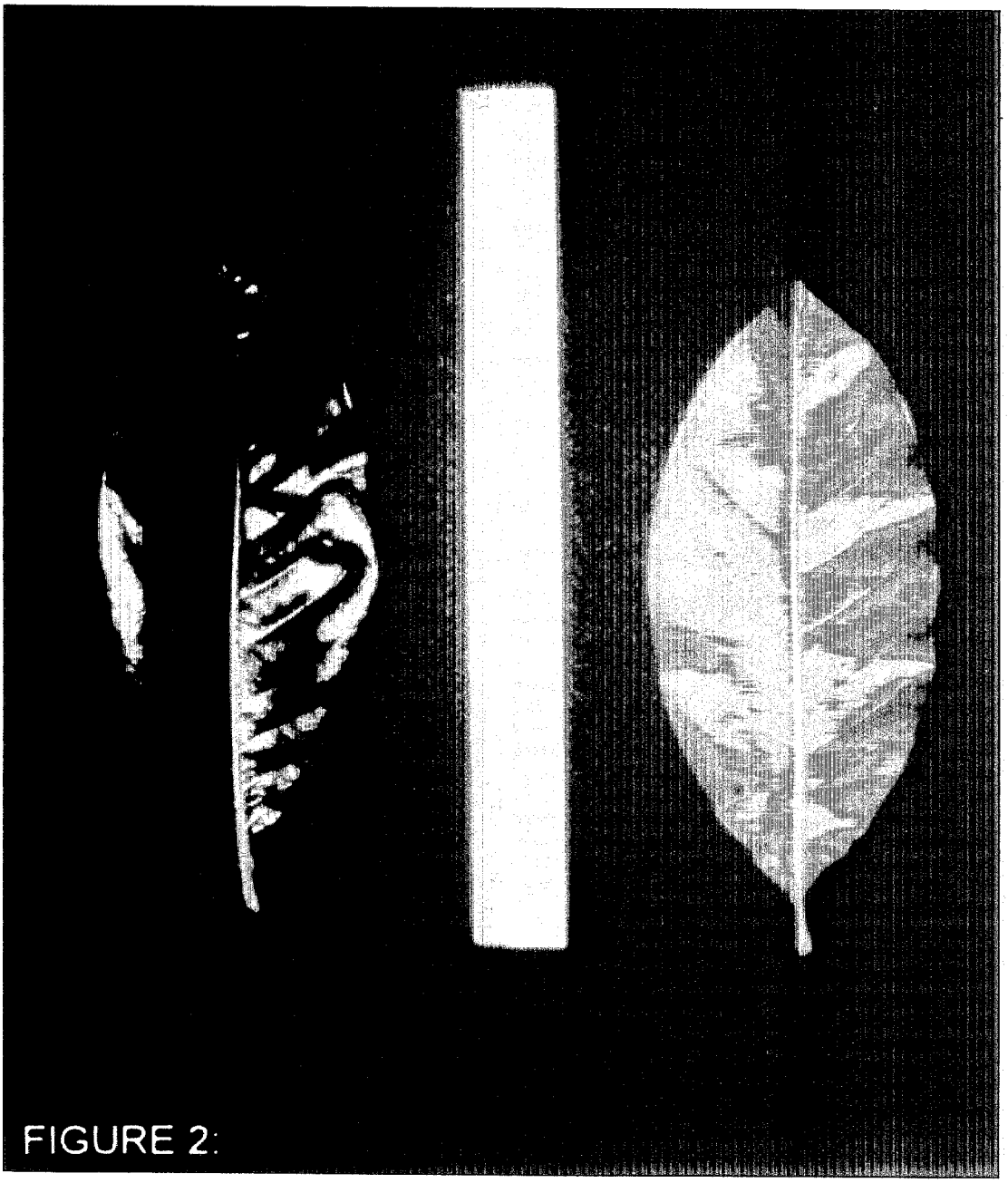
FIG. 2 shows the front and rear sides of a mature one year old leaf with the front side being the upper leaf while the rear side is shown in the bottom leaf.

It will be noted that the colors on both the front and rear sides are green.

DESCRIPTION OF THE NEW PLANT

The following is a detailed description of our new *Magnolia grandiflora* based upon observations of a tree growing in the Westervelt Tree Company nursery for the past 7 years. The observations have been made over a period of time since 1987 at Selma, Ala. and at another test nursery in Lexington, Ky. The color designations being used throughout this specification are based on the Munsell Color System derived from electronic evaluation using a Minolta Spectrophotometer CM 2002.

Origin: Seedling.

Parentage: Unknown. The originally observed seedling originate din a bed of seedlings *Magnolia grandiflora.* The original seeds for this bed resulted from the open pollination of a number of southern magnolias.

Classification:

*Botanic.—Magnolia grandiflora.*

*Commercial.*—Southern Magnolia.

Form: Tall evergreen tree of pyramidal habit with a straight and strong central trunk. Blunt, broad, flame shape.

Height: In a period of six to seven years, rooted cuttings of the new plan have reached an average height of 10 to 12 feet with a trunk size of 3 to 4 inches. The growth rate is normally about 2 to 4 feet per year.

The plant maintains a dense habit and exhibits very abundant branch development. The foliage is dense, coarse textured, and exhibits little no pubescence. The branch structure is also defined as a coarse, dense branch structure. The current season's bark is smooth and green in color. Mature bark has a slight texture and is brown to reddish-brown in color.

Cold tolerance: The tree has survived 8° F. in February 1995 with no apparent damage.

Branching: The branching is coarse with numerous, closely spaced branches diverging at an angle of approximately 45 degrees from the central trunk. The upswept branches create a columnar or pyramidal form with a dense, compact crown. The shape and growth habit described are based upon specimens not subjected to pruning or other cultural practices that might otherwise influence the shape or growth habit of the trees. Further, the trees used for asexual propagation stock were isolated for observation purposes.

Foliage: The leaves are glossy green on top and light green on bottom. Bottoms of leaves are most glabrous with some ferrugineous pubescence. Leaves are an oblong or elliptical shape and slightly undulate surface. Bases are rounded, margins entire and apices acuminate. The size of mature leaves ranges from 7 to 9 inches long to 3 to 4.5 inches wide. The undersides of the leaves exhibit little pubescence, as shown in the photographs, unlike other varieties of *Magnolia grandiflora* which are characterized by a great abundance of pubescence and a brown leaf color. Petioles are ½ to 1 inch long.

Color: According to the Munsell Color System, upper leaf surfaces have a hue ranging from 6.1gy to 6.6gy, value of 3.2 and chroma of 2.3. The back surfaces have a hue of 2.6gy to 7.0gy, value of 4.2 to 4.5 and a chroma of 3.2. Trunk color has an average hue of 6.8gy, value of 4.2 and chroma 3.7.

Stems: Young stems, between one and two years old, are stout, strong and are approximately ¼ to ½ inches in diameter with pubescence new growth and dark green older stems. A distinctive circular scale scar is present at each node.

Buds: The parent plant of this new plant has yet to produce flowers and only one flower bud has appeared, notwithstanding the numerous provocations. Terminal buds are about 1 inch long, curved at the apex, and are covered in a single pubescent scale. Lateral buds are smaller but prominent ¼ inch ovoid shaped buds.

Flowers: The new plant is characterized by a lack of flowers. The tree's low propensity to flower is believed to have a genetic basis. This tree variety has been compared to other *Magnolia grandiflora* seedlings and cultivars of comparable age, grown under identical environmental conditions and with identical cultural practices. A marked difference in the propensity to flower has been observed when making this comparison in that the Green Giant Southern Magnolia has exhibited little to no flowering, while at the same time showing a remarkable rate of growth. It is recognized that this vigorous growth may be in lieu of flower production. However, the above mentioned comparison indicates that this tree's lack of flowering may well have a genetic base since the other trees, under the same growing conditions, showed flowering consistent with the species. It is possible that more flowering may be observed when planted in a less growth oriented environment.

In general, the outstanding characteristics of our new variety of *Magnolia grandiflora,* which distinguish it from other varieties of southern magnolia and all other types of magnolias, resides in its dense growth with large glossy leaves which are green on both sides and exhibit minimal pubescence, as well as the coarse textured, broad, blunt, flame shaped tree and dense foliage. It has a strong, dominant central leader which is a beneficial trait for commercial production.

Our new *Magnolia grandiflora* is easy to root from cuttings collected in July and early August which also provides commercial appeal and assures trueness-to-type. The rapid growth rate under normal fertilizer and moisture conditions, together with its very abundant branch development, assures that the plant will always maintain a very dense habit.

I claim:

1. The new and distinct cultivar of *Magnolia grandiflora,* substantially as herein shown and described, characterized by a coarse textured, broad, blunt, flame shape and by a pyramidal growth habit with a fairly coarse branch structure, and its dense foliage of coarse textured, green backed leaves exhibiting little pubescence and by exhibiting little to no flowering.

* * * * *